United States Patent [19]

Kuoni

[11] Patent Number: 5,593,446
[45] Date of Patent: Jan. 14, 1997

[54] ANCHORING SHAFT FOR JOINT ENDOPROSTHESIS

[76] Inventor: Xaver Kuoni, Alter Zurichweg 33, 8952 Schlieren, Switzerland

[21] Appl. No.: 423,443

[22] Filed: Apr. 19, 1995

[30] Foreign Application Priority Data

Nov. 9, 1994 [CH] Switzerland ............... 03355/94

[51] Int. Cl.$^6$ ........................................ A61F 2/30
[52] U.S. Cl. .................. 623/18; 623/20; 623/22; 623/23
[58] Field of Search ............. 623/18, 16, 21–23; 606/62, 66, 67, 72, 95

[56] References Cited

U.S. PATENT DOCUMENTS

| | | | |
|---|---|---|---|
| 3,996,625 | 12/1976 | Noiles | 623/18 |
| 4,242,759 | 1/1981 | White | 623/21 |
| 4,261,063 | 4/1981 | Blanquaert | 623/18 |
| 4,261,351 | 4/1981 | Scherfel | 606/62 |
| 4,549,319 | 10/1985 | Meyer | 623/18 |
| 4,624,673 | 11/1986 | Meyer | 623/16 |
| 4,695,283 | 9/1987 | Aldinger | 623/16 |
| 4,784,124 | 11/1988 | Kaltenbrunner et al. | |
| 4,846,839 | 7/1989 | Noiles | 623/18 |
| 4,944,761 | 7/1990 | Stuhmer et al. | |
| 5,007,932 | 4/1991 | Bekki et al. | 623/21 |
| 5,108,453 | 4/1992 | Kotz et al. | |
| 5,133,770 | 7/1992 | Zweymuller et al. | 623/16 |
| 5,326,366 | 7/1994 | Pascarella et al. | 623/21 |
| 5,370,695 | 12/1994 | Meuli et al. | 623/16 |

FOREIGN PATENT DOCUMENTS

| | | |
|---|---|---|
| 0209516 | 1/1987 | European Pat. Off. . |
| 0378044 | 7/1990 | European Pat. Off. . |
| 0390768 | 10/1990 | European Pat. Off. . |
| 0427902 | 3/1994 | European Pat. Off. . |
| 02839092 | 3/1980 | Germany . |
| 0474351 | of 1952 | Italy .................. 623/23 |
| WO83/02555 | 8/1983 | WIPO . |

*Primary Examiner*—Debra S. Brittingham
*Assistant Examiner*—Bruce E. Snow
*Attorney, Agent, or Firm*— Oliff & Berridge

[57] ABSTRACT

An anchoring shaft for a joint endoprosthesis includes a rectilinear core. The core is provided with a shape tapering towards a distal end and a series of sawtooth-shaped teeth. The teeth are formed by ribs which extend in a longitudinal direction of the shaft. The ribs have a rectangular cross-section and a uniform thickness along their length. The teeth are defined as a long tooth flank and with a short, steep tooth flank. The shaft is usable for many joint endoprosthesis, including hip joint prosthesis.

21 Claims, 1 Drawing Sheet

ANCHORING SHAFT FOR JOINT ENDOPROSTHESIS

BACKGROUND OF THE INVENTION

1. Field of the Invention

The invention relates to an anchoring shaft for a joint endoprosthesis. More specifically, the anchoring shaft is used in a hip joint prosthesis.

2. Description of Related Art

An anchoring shaft is disclosed in EP-A-0 427 902. The shaft disclosed in the European application includes a femoral head prosthesis. The cross-section of the shaft is square in the distal or lower half. The proximal or upper half of the shaft has a rounded rectangular or oval shape. The shaft widens conically on all sides of the shaft starting from the distal end.

The European application prefers a square shaped shaft at the distal end, since semicircular interstices establish areas where cancellous bone tissue can form and revascularization of the bone takes place. The edges of the lower half of the shaft are provided with sawtooth-shaped teeth. The points of the teeth lie on an edge and are slightly set back. The teeth are short with a very small tooth depth, so an approximate square cross-section of the shaft is retained. The teeth are provided in rows and point in a medial direction. The teeth of some rows can be designed so they perform a cutting action. The teeth in other tooth rows are designed so they do not cut, but merely displace bone tissue. Accordingly, the supporting action of the square shaft along the edges is maintained.

SUMMARY OF THE INVENTION

It is an objective of the invention to provide an anchoring shaft for a joint endoprosthesis which can be effortlessly driven into a prepared bone cavity, while avoiding damaging the bony substance. In addition, it is an objective of the invention to provide an anchoring of the endoprosthesis in the bone which is as stable as possible, to prevent loosening as a result of the normal loading of the joints.

The invention achieves the objectives by providing an anchoring shaft having a core. Ribs are provided on the core and the ribs have cutting surfaces in the form of sawtooth-shaped teeth. The teeth protrude beyond the core of the anchoring shaft. The cutting surfaces are aligned in the longitudinal direction and can be driven relatively easily into the bone. Thus, the ribs of the anchoring shaft are directly surrounded by bony substance, so an excellent anchoring is achieved.

The teeth engage the bony substance with steep tooth flanks pointing distally, to prevent the anchoring shaft from sinking further into the bone. Since the ribs of the anchoring shaft have a uniform thickness along their entire length, no lateral splitting forces develop during implantation of the shaft. Thus, the bone tissue is not forced open during the implantation.

Further objectives of the present invention are evident from the following description.

BRIEF DESCRIPTION OF THE INVENTION

Preferred embodiments are described with reference to the drawing, in which like reference characters denote like elements throughout the figures, and in which.

DETAILED DESCRIPTION OF THE PREFERRED EMBODIMENT

Figure 1:
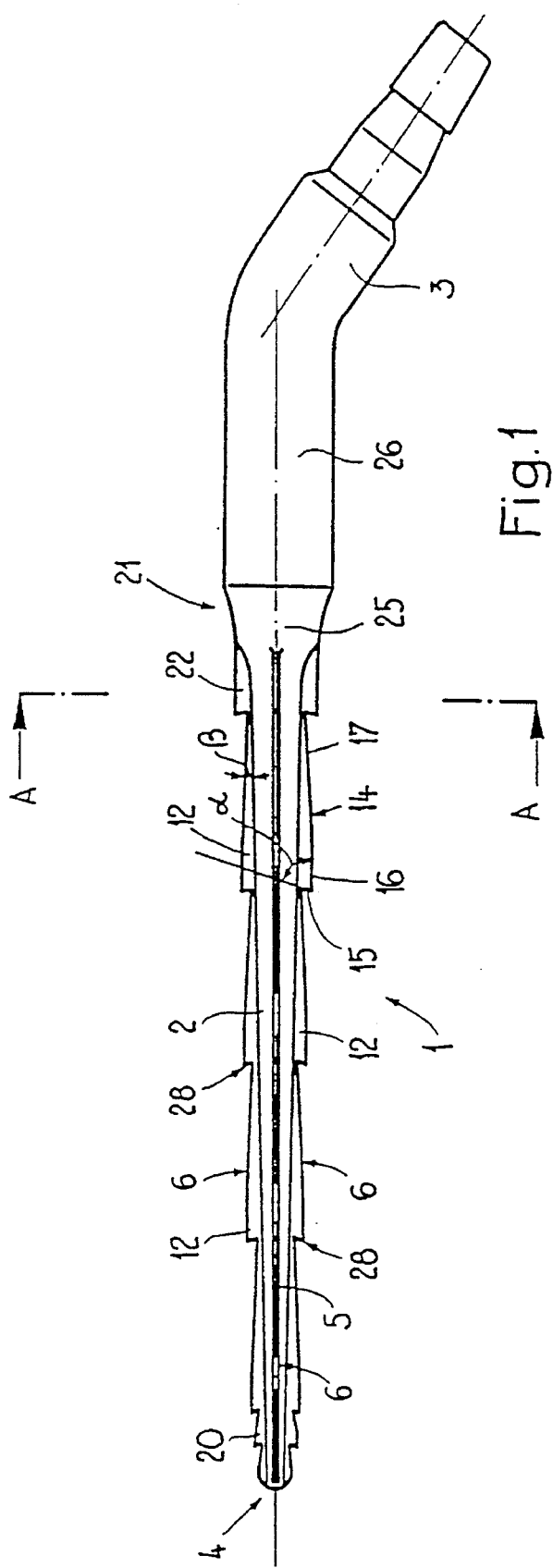
FIG. 1 shows a side view of an anchoring shaft for a joint endoprosthesis.
Figure 2:
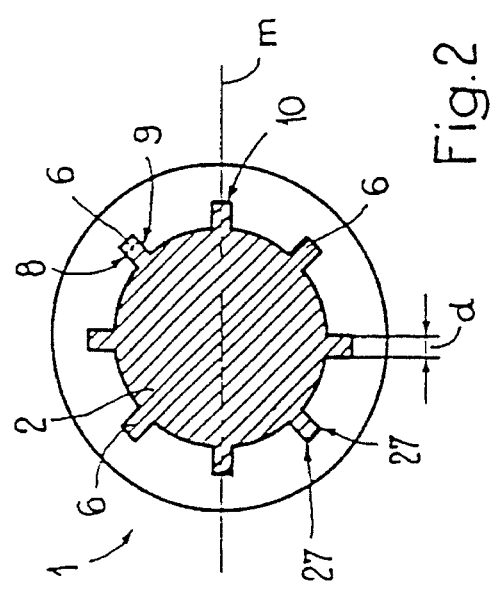
FIG. 2 shows a cross-section along the line A—A in FIG. 1.

FIGS. 1 and 2 show an anchoring shaft 1 of a hip joint prosthesis. The shaft 1 includes a rectilinear core 2 and an angled attachment part 3 for receiving a ball-shaped joint head (not shown). As seen in FIG. 2, the core 2 has a circular cross-section conically tapering towards a distal end 4. Ribs 6 extend in the longitudinal direction of the shaft 1. The ribs 6 protrude radially outward and have two parallel side surfaces 8 and 9. As seen in FIG. 2, the ribs have a uniform thickness d along the entire length. The ribs 6 are equally spaced from each other.

The end face 10 of each rib 6 is planar and is positioned at right angles to the respective mid-plane m of the rib 6. The rib 6 has sawtooth-shaped teeth 12 in its middle area. Some of the sawtooth-shaped teeth 12 are of different lengths. Each tooth 12 has a long tooth flank 14 and a short or steep tooth flank 15, which define an angle $\alpha$. The angle $\alpha$ is slightly smaller than 90°.

The long tooth flank 14 has a short part 16, which is parallel to the circumference of the core 2 and a longer part 17 which is angled with respect to short part 16. Long part 17 defines an acute angle B of less than about 30°, with respect to the longitudinal direction of the core 2.

A short tooth 20 is provided on each rib 6 proximate the distal end 4. Tooth 20 has the same shape as teeth 12.

Each rib 6, near the proximal end 21 of the core, is provided with a tooth section 22. Tooth section 22 has a similar shape as teeth 12, however it is larger and merges into a conically widened transition piece 25 of the core 2, after about a third of its length. Transition piece 25 then merges, gradually rounding into a cylindrical part 26. Cylindrical part 26 is joined to the angled attachment part 3. The cylindrical part 26 has a greater diameter than that of the core 2.

The edges 27 of the rib 6, between the side surfaces 8 and 9 and the end face 10, form sharp edges. As seen in FIG. 2, the sharp edges 27 constitute a cutting edge. This cutting edge structure is provided on at least the short tooth flank 15 of teeth 12, 20 and 22. A similar cutting edge structure can also be provided on the long tooth flank 14. In either situation, the points of the teeth 12, 20 and 22, located between the long tooth flank 14 and the short tooth flank 15, also form a sharp point.

The anchoring shaft 1 is normally produced using a known protheses material in one piece and is unitary. The short or steep tooth flanks 15 of ribs 6 prevent the anchoring shaft 1 from sinking into the bone tissue. This sinking prevention is of great importance due to loads normally subjected on a joint. The anchoring shaft 1 can be stabilized in a bone, as a result of the relatively narrow ribs 6. The stabilization is quickly achieved once the joint endoprosthesis has been surgically implanted.

The anchoring shaft 1 with the ribs 6 is suitable, not only for a hip joint prosthesis, but also for other joint endoprosthesis such as elbow or ankle joint prostheses. Further, the simple configuration of the anchoring shaft 1 with the ribs 6 can be used as a replacement for existing joint endoprosthesis, because of the design of the cutting edges of the teeth.

The design of the teeth cutting edges, such as the edges 27 and the teeth points 28, does not force bone tissue open when the anchoring shaft 1 is driven into a hollowed out cavity in the bone.

While this invention has been described in conjunction with specific embodiments thereof, it is evident that many alternatives, modifications and variations will be apparent to those skilled in the art. Accordingly, the preferred embodiment of the invention as set forth herein are intended to be illustrative, not limiting. Various changes may be made without departing from the spirit and scope of the invention as defined in the following claims.

What is claimed is:

1. An anchoring shaft for a joint endoprosthesis, the shaft comprising:

a rectilinear core having longitudinal axis, a distal end and an attachment end, the core tapering inwardly toward the distal end and having a cross-section symmetrical with respect to the longitudinal axis;

a plurality of ribs provided on the core, each rib protruding from the core in a radial direction and extending in the longitudinal direction of the core from the distal end toward the attachment end, each rib having a rectangular cross-section and a uniform thickness; and a plurality of teeth provided on each rib, each tooth being defined by a flank and a steep flank, each flank extending essentially in the longitudinal direction of the associated rib and ascending in the direction of the distal end, each steep flank extending from the flank toward the core to define a tooth point, each steep flank having a surface facing the distal end of the core.

2. A shaft according to claim 1, wherein the flank extends from the core in the longitudinal direction for a first distance and the steep flank extends from the flank towards the core in a second direction for a second distance, wherein the first distance is longer than the second distance.

3. A shaft according to claim 2, wherein the flank and the steep flank define an angle at the tooth point slightly less than 90°.

4. A shaft according to claim 1, wherein the core has a generally circular cross-section.

5. A shaft according to claim 1, wherein the plurality of ribs are uniformly distributed on the core.

6. A shaft according to claim 1, wherein the plurality of ribs are equally spaced from each other.

7. A shaft according to claim 1, wherein the plurality of ribs being arranged in a plurality of rows.

8. A shaft according to claim 7, wherein the plurality of rows includes at least two rows.

9. A shaft according to claim 8, wherein the plurality of rows includes six rows.

10. A shaft according to claim 1, wherein the distal end of the core is generally circular in cross-section.

11. A shaft according to claim 1, wherein the flank defines an acute angle with the longitudinal axis of the core.

12. A shaft according to claim 11, wherein the acute angle is less than 30°.

13. A shaft according to claim 1, wherein each flank closest to the distal end is a distal flank, the distal flank being shorter than the other flanks, and wherein each tooth closest to the distal end of the shaft is defined by a distal flank and a steep flank.

14. A shaft according to claim 1, wherein each flank closest to the attachment end is an attachment flank, the attachment end includes a transition piece, and each tooth closest to the attachment end is defined by the attachment flank that merges into the transition piece and a steep flank.

15. A shaft according to claim 14, wherein the transition piece gradually tapers outwardly from the core to the attachment piece.

16. A shaft according to claim 15, wherein the attachment piece includes a cylindrical part, the transition piece being connected to the cylindrical part of the attachment piece.

17. A shaft according to claim 15, wherein the transition piece has a generally circular cross-section and has a greater diameter than the core, and the transition piece has a smaller diameter than the attachment end.

18. A shaft according to claim 1, wherein the shaft is unitary and integrally constructed from one piece of material.

19. A shaft according to claim 1, wherein the attachment end is angled and adapted to receive a ball-shaped joint head.

20. A shaft according to claim 1, wherein the distal end of the shaft is rounded.

21. A shaft according to claim 1, wherein the core and the plurality of ribs are integrally formed.

* * * * *